US009717487B2

(12) United States Patent
White et al.

(10) Patent No.: US 9,717,487 B2
(45) Date of Patent: Aug. 1, 2017

(54) BIOADHESIVE MIXING AND PREPARATION SYSTEMS AND METHODS USING TWO SYRINGES

(71) Applicant: St. Jude Medical Puerto Rico LLC, Caguas, PR (US)

(72) Inventors: Troy T. White, Maple Grove, MN (US); Zachary J. Tegels, Minneapolis, MN (US); Edward E. Parsonage, St. Paul, MN (US); Russell D. Terwey, St. Michael, MN (US); Martha Escobar, Jordan, MN (US); Timothy M. McGlinch, St. Paul, MN (US); Bernhard Kaeferlein, Champlin, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 1151 days.

(21) Appl. No.: 13/779,031

(22) Filed: Feb. 27, 2013

(65) Prior Publication Data

US 2014/0135831 A1    May 15, 2014

Related U.S. Application Data

(60) Provisional application No. 61/726,265, filed on Nov. 14, 2012.

(51) Int. Cl.
*A61B 17/00* (2006.01)
*A61B 17/22* (2006.01)

(52) U.S. Cl.
CPC .... *A61B 17/00491* (2013.01); *A61B 17/0057* (2013.01); *A61B 2017/0065* (2013.01);
(Continued)

(58) Field of Classification Search
CPC .... A61B 17/00491; A61B 2017/00495; A61B 2017/0065; A61M 3/005; A61J 1/201;
(Continued)

(56) References Cited

U.S. PATENT DOCUMENTS 3,563,373 A    2/1971  Paulson
4,619,651 A *  10/1986 Kopfer .................. A61J 1/2096
                                                                 604/414

(Continued)

FOREIGN PATENT DOCUMENTS

EP    0292472 A1    11/1988
EP    1849448 A1    10/2007
(Continued)

OTHER PUBLICATIONS

U.S. Appl. No. 13/770,586, filed Feb. 19, 2013.
(Continued)

*Primary Examiner* — Sarah W Aleman
(74) *Attorney, Agent, or Firm* — Holland & Hart

(57) ABSTRACT

A bioadhesive mixing assembly includes first and second syringes and an adapter. The first syringe includes first and second chambers holding a first sealant component and an activator, respectively. The second syringe includes third and fourth chambers holding a second sealant component and one of an activator or a third sealant component, respectively. The adapter is mounted to the first syringe and includes first and second channels in flow communication with the first and second chambers, a first seal member providing sealed access to the first and second channels, first and second needles connected in flow communication with the third and fourth chambers, and a second seal member enclosing the first and second needles. Connecting the adapter to the second syringe punctures the first and second seal members with the first and second syringes to create
(Continued)

flow communication between the first and third chambers and the second and fourth chambers.

23 Claims, 9 Drawing Sheets

(52) U.S. Cl.
CPC .............. *A61B 2017/00495* (2013.01); *A61B 2017/22067* (2013.01)

(58) Field of Classification Search
CPC ...... A61J 1/2065; A61J 1/2089; A61J 1/2093; A61J 1/2096
See application file for complete search history.

(56) References Cited

U.S. PATENT DOCUMENTS

| | | | | |
|---|---|---|---|---|
| 4,743,229 | A | * | 5/1988 | Chu ..................... A61F 2/4644 604/110 |
| 6,471,670 | B1 | * | 10/2002 | Enrenfels ......... A61B 17/00491 604/191 |
| 7,322,956 | B2 | * | 1/2008 | Fehr ..................... A61O 5/064 366/268 |
| 8,333,787 | B2 | | 12/2012 | Pipenhagen et al. |
| 8,506,592 | B2 | | 8/2013 | Killion et al. |
| 2008/0199513 | A1 | * | 8/2008 | Beretta ............ A61B 17/00491 424/443 |
| 2011/0166595 | A1 | | 7/2011 | Vidlund et al. |
| 2011/0282383 | A1 | | 11/2011 | Vidlund et al. |
| 2013/0006299 | A1 | | 1/2013 | Pipenhagen et al. |
| 2013/0190808 | A1 | | 7/2013 | Tegels et al. |
| 2013/0190812 | A1 | | 7/2013 | Vidlund |
| 2013/0190813 | A1 | | 7/2013 | Tegels et al. |

FOREIGN PATENT DOCUMENTS

| | | |
|---|---|---|
| EP | 2036529 A1 | 3/2009 |
| WO | 9746202 A1 | 12/1997 |

OTHER PUBLICATIONS

U.S. Appl. No. 13/770,714, filed Feb. 19, 2013.
U.S. Appl. No. 13/772,834, filed Feb. 21, 2013.
U.S. Appl. No. 13/773,062, filed Feb. 21, 2013.
U.S. Appl. No. 13/773,206, filed Feb. 21, 2013.
PCT International Search Report for International Application No. PCT/US2013/027850, mailed Sep. 27, 2013 (7 pp.).

* cited by examiner

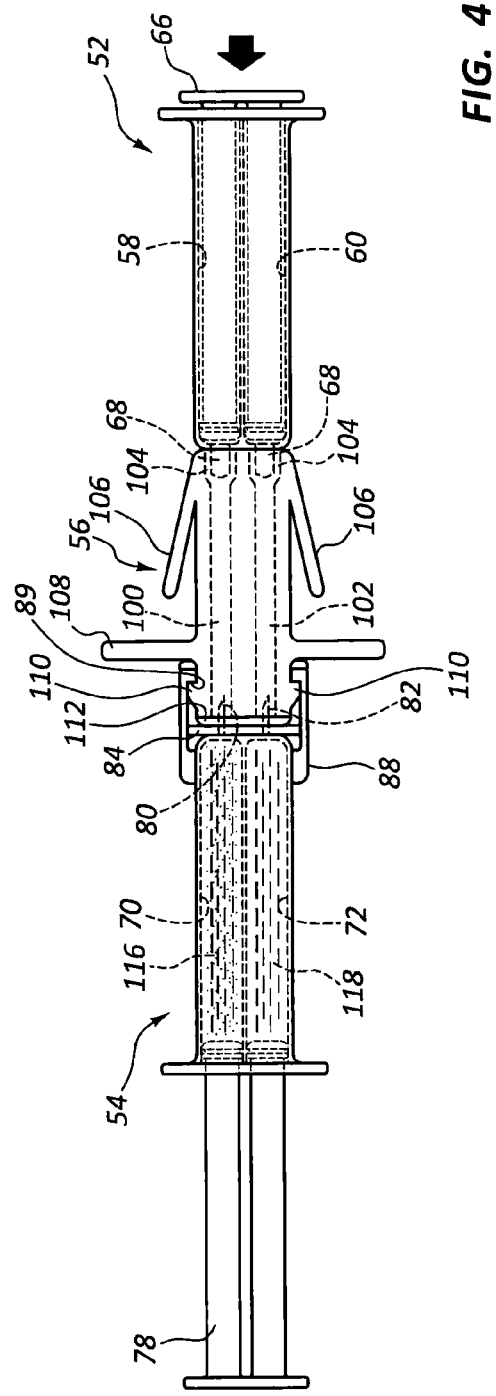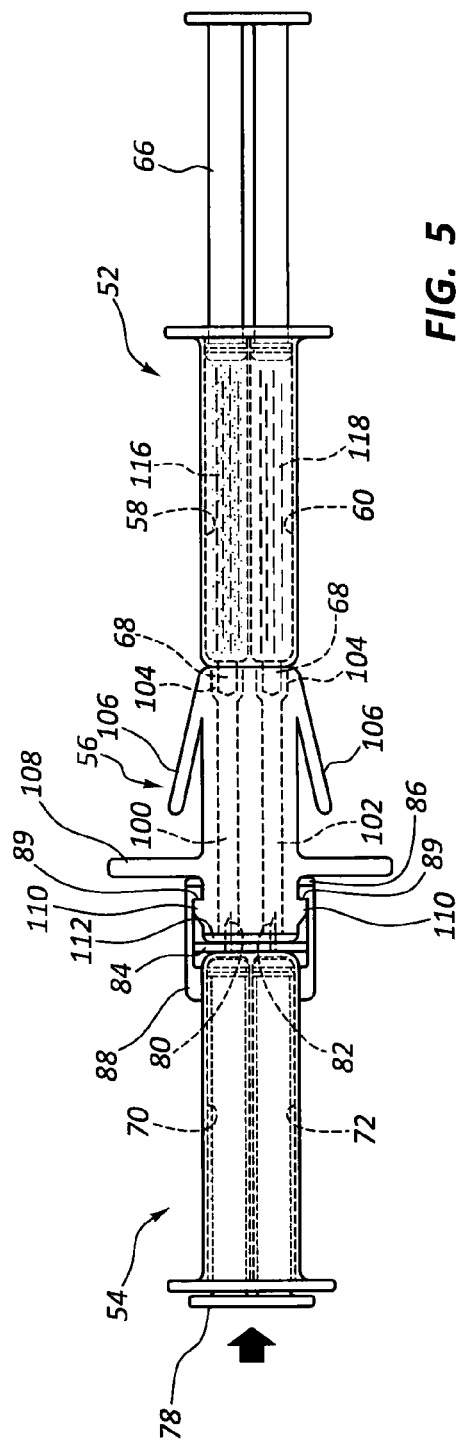

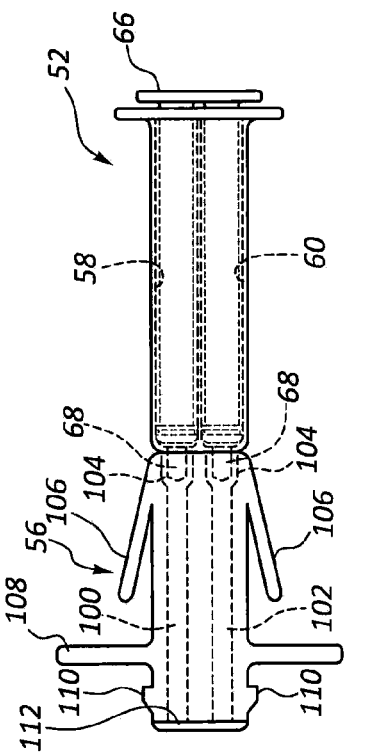
FIG. 6
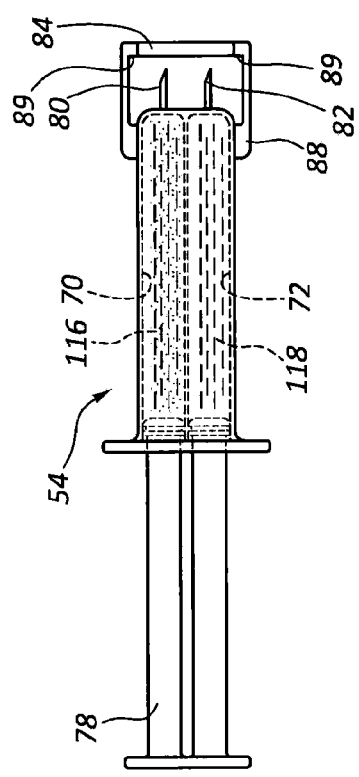
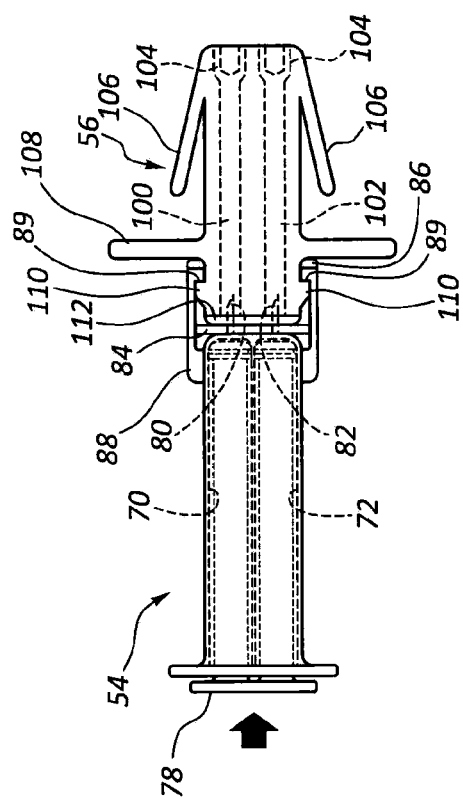
FIG. 7

BIOADHESIVE MIXING AND PREPARATION SYSTEMS AND METHODS USING TWO SYRINGES

RELATED APPLICATION

This claims the benefit of U.S. Provisional Application No. 61/726,265, filed 14 Nov. 2012 which is hereby incorporated by reference herein in its entirety.

TECHNICAL FIELD

The present disclosure relates generally to methods and systems for sealing tissue punctures, and more particularly, to methods and systems for mixing a bioadhesive sealant in preparation for delivering the mixed bioadhesive sealant to a tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one primary problem is insuring a complete seal of the puncture. One technique includes the use of a bioadhesive material to seal the puncture. Some types of bioadhesive materials must be activated prior to use, and should be activated just prior to use in order to avoid premature activation of the bioadhesive material. The handling and activation of bioadhesive materials for use in vascular and other tissue puncture closure applications present a number of challenges, particularly when using bioadhesive sealant components that have a quick set time.

SUMMARY

One aspect of the present disclosure relates to a bioadhesive mixing assembly that includes first and second syringes and an adapter. The first syringe includes first and second chambers holding a first sealant component and an activator, respectively. The second syringe includes third and fourth chambers holding a second sealant component and one of another activator or a third sealant component, respectively. The adapter is mounted to the first syringe and includes first and second channels in flow communication with the first and second chambers, a first seal member providing sealed access to the first and second channels, first and second needles connected in flow communication with the third and fourth chambers, and a second seal member enclosing the first and second needles. Connecting the adapter to the second syringe punctures the first and second seal members with the first and second syringes to create flow communication between the first and third chambers and the second and fourth chambers.

One of the first and second sealant components may be stored under vacuum pressure. The sealing members may include a rubber septum. The adapter and second syringe may be connected together with a snap-fit connection. Flow communication may be created between the first and second syringes by relative longitudinal movement between the adapter and second syringe. The bioadhesive mixing assembly may further include a first removable foil cap positioned on the first sealing member, and a second removable foil cap positioned on the second sealing member. The first sealant component may include acrylate, and the second sealant component may include one of PEG and thiol. The adapter may include at least one release tab to releasably connect the adapter to one of the first and second syringes. Operating at least one of the first and second syringes mixes the first and second sealant components together, and mixes the activator and one of the another activator or the third sealant component.

Another aspect of the present disclosure relates to a vascular closure system that includes a sealant delivery device and a sealant mixing device. The sealant delivery device includes a delivery tube and a sealant manifold. The sealant mixing assembly includes a first syringe carrying at least a first sealant component, a second syringe carrying at least a second sealant component, an adapter connected to the first syringe and in flow communication with the first sealant component, a first rupturable seal carried by the adapter and configured to be ruptured upon connecting the adapter to the second syringe, and a second rupturable seal carried by the second syringe and configured to be ruptured upon connecting the adapter to the second syringe. The sealant mixing assembly is operable to mix the first and second sealant components, store the mixed first and second sealant components in at least one of the first and second syringes, and deliver the mixed first and second sealant components to the sealant delivery device via connection to the sealant manifold.

At least one of the first and second rupturable seals may include a rubber septum. The tissue puncture closure device may include first and second needles carried by one of the adapter and the second syringe, wherein the first and second needles are configured to rupture the first and second seals upon connecting the adapter to the second syringe. Each of the first and second syringes may store the mixed first and second sealant components. At least one of the first and second syringes may carry a sealant component under vacuum. The adapter and second syringe may be connected with a snap-fit connection. The first and second syringes may be releasably connected to the adapter.

Another aspect of the present disclosure relates to a method of delivering sealant to a tissue puncture. The method includes providing a sealant delivery device and sealant mixing device, the sealing delivery device comprising a delivery tube insertable into a tissue puncture, the sealant mixing device comprising an adapter and first and second syringes, the first syringe holding at least a first sealant component, and the second syringe holding at least a second sealant component. The adapter includes a first sealing member and the second syringe includes a second sealing member. The method also includes connecting the adapter in fluid communication with the first syringe, connecting the adapter to the second syringe to rupture the first and second sealing members, wherein rupturing the first and second sealing members connects the first and second syringes in flow communication to mix the first and second sealing components. The method includes disconnecting one of the first and second syringes from the adapter, wherein the one of the first and second syringes carrying the mixed first and second sealant components, connecting the one of the first and second syringes in flow communication with the delivery tube, and delivering the mixed first and second sealant components through the delivery tube to the tissue puncture.

Connecting the adapter to the second syringe may include providing a snap-fit connection between the adapter and the second syringe. At least one of the adapter and the second syringe may include at least one needle, and connecting the adapter to the second syringe ruptures the first and second sealing members with the at least one needle. The adapter may be releasably connected to at least one of the first and second syringes.

Another example method relates to preparing bioadhesive sealant for use in sealing a tissue puncture. The method includes providing first and second syringes and an adapter, the first syringe carrying at least a first sealant component and the second syringe carrying at least a second sealant component, wherein the second syringe comprises a first seal and the adapter comprising a second seal. The method also includes connecting the first syringe with the adapter to provide flow communication between the adapter and the first syringe, connecting the second syringe with the adapter to concurrently breach the first and second seals to create flow communication between the first and second syringes, and mixing the first and second sealant components.

Mixing the first and second components may include operating at least one of the first and second syringes. The method may also include providing a first removable foil cap positioned on the first sealing member, and a second removable foil cap positioned on the second sealing member, and removing the first and second removable foil caps before connecting the second syringe with the adapter.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1A is a cross-sectional view of a portion of the vascular closure system of FIG. 1 taken along cross-section indicators 1A-1A.

FIG. 1B is a cross-sectional view of a portion of the vascular closure system of FIG. 1 taken along cross-section indicators 1B-1B.

FIG. 4 shows the sealant mixing assembly of FIG. 3 with all of the sealant components moved into one syringe.

FIG. 5 shows the sealant mixing assembly of FIG. 3 with all of the sealant components in another one of the syringes.

FIG. 6 shows the sealant mixing assembly of FIG. 4 with the syringe holding all of the sealant components detached and prepared for ejecting the sealant components into a sealant delivery device of the vascular closure system of FIG. 1.

FIG. 7 shows the sealant mixing assembly of FIG. 5 with the syringe holding all of the sealant components detached and prepared for delivering the sealant components to the sealant delivery device of the vascular closure system of FIG. 1.

Throughout the drawings, identical reference numbers designate similar, but not necessarily identical, elements.

DETAILED DESCRIPTION

Figure 1:
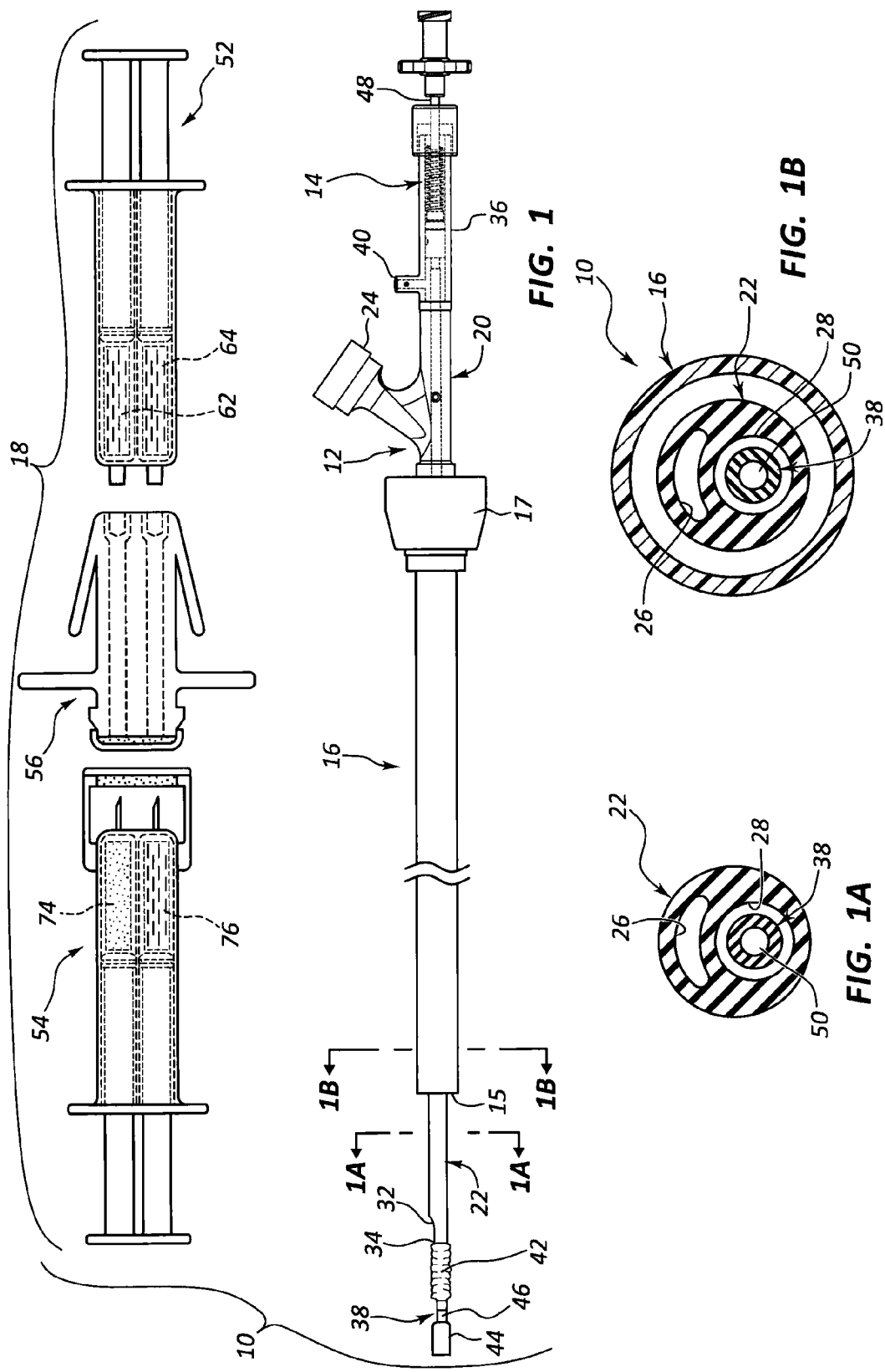
FIG. 1 is an exploded view of an example vascular closure system in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

One example of the present disclosure is directed to a vascular closure system configured to deliver a volume of flowable bioadhesive sealant (the "bioadhesive" or "sealant") to a vessel puncture to seal the vessel puncture. The bioadhesive may be prepared prior to delivering the bioadhesive to the vessel puncture. A sealant mixing assembly may be used to mix some components of the bioadhesive and store the mixed components in a syringe or other applicator. The syringe is then attached to a sealant delivery device for use in delivering the bioadhesive to the vessel puncture.

In one embodiment, the sealant mixing assembly includes a first dual chamber syringe (also referred to as a procedural syringe) that carries PEG or thiol powder in one of the chambers, and an activator component, solution of an acrylate component, or nothing in the other chamber. The sealant mixing assembly also includes a second dual chamber syringe (also referred to as a preparation syringe) that carries a solution of acrylate component in one chamber and an activator, dissolution buffer for the thiol, or nothing in the other chamber. One chamber of either the first or second syringe carries an activator. The sealant mixing assembly also includes an adaptor that interfaces between the first and second syringes. The adaptor may be configured to releasably attach the first and second syringes to the adaptor. The adaptor may provide for fluid transfer between the first and second syringes.

In one embodiment, the adapter is first connected to the first syringe. The second syringe is later connected to the adaptor. In at least one example, connecting the second syringe to the adaptor concurrently provides for fluid communication between chambers of the first and second syringes. Typically, the sealant components of the second syringe are drawn into chambers of the first syringe, and the first syringe is then detached from the adaptor and used to deliver the mixed sealant components to a sealant delivery device. Other arrangements are possible such as, for example, providing a mixture of the sealant components in both of the first and second syringes and disconnecting the first and second syringes from the adaptor so that the first and second syringes can be separately used to deliver the mixture of sealant components to a sealant delivery device. A still further example includes advancing all of the sealant components into the second syringe and detaching the second syringe from the adaptor so that the second syringe can be used to deliver the mixed sealant components to a sealant delivery device.

The adaptor may include a first sealing member that maintains the internal flow channels of the adaptor (which are in flow communication with chambers of the first syringe) sterile prior to connecting the adaptor to the second syringe. The second syringe may include a second sealing member that maintains the contents of the second syringe sterile prior to connecting the second syringe to the adaptor. The first and second sealing members may be punctured or ruptured concurrently with connecting the second syringe to the adaptor. In one example, one of the adaptor and second syringe carries at least one needle that operates to puncture the first and second sealing members upon connecting the second syringe to the adaptor. The first and second sealing members may be covered with a removable foil cap that provides additional sterility and inhibits transfer of moisture through the sealing member. In some arrangements, a separate needle is used for each flow channel through the adaptor or each chamber of the second syringe.

At least one of the adaptor and first syringe may also carry at least one needle that provides flow communication between the adaptor and first syringe upon connecting the adaptor to the first syringe. Many other types of interfaces may be used besides needles to provide flow communication between the adaptor and the first and second syringes.

The first and second sealing members may each comprise a rubber septum or other material that can be punctured or ruptured. The cap may comprise foil or other materials that provide an additional barrier. Other structures may be used to maintain separation and sterility of the sealant components carried by the first and second syringes and the adaptor.

Referring now to FIGS. 1-1B, an example vascular closure system 10 is shown including a sealant delivery device 12, a balloon location device 14, a sheath 16, and a sealant mixing assembly 18. The sealant delivery device 12, balloon location device 14, and sheath 16 are shown assembled together in an arrangement that would be used when the vascular closure system 10 is prepared for delivering a volume of sealant (e.g., bioadhesive) to a vessel puncture (e.g., see FIGS. 10-12). The sealant mixing assembly 18 is shown unassembled prior to mixing of sealant components carried by the first and second syringes of the sealant mixing assembly 18.

The sealant delivery device 12 includes a manifold 20 and a dual lumen tube 22. The manifold 20 includes an injection port 24. The dual lumen tube 22 includes first and second lumens 26, 28. The first lumen 26 includes a distal open end 32. The second lumen 28 includes a distal end 34. The first lumen 26 is configured for delivery of a sealant to a vessel puncture. The second lumen 28 is configured to receive a portion of the balloon location device 14. In some arrangements, a separate volume of sealant may be delivered through the second lumen 28 to a vessel puncture.

The balloon location device 14 includes a housing 36, an inner tube 38, an inflation port 40, a balloon 42, and a detachable tip 44. The inner tube 38 may include distal and proximal ends 46, 48, and an inner tube lumen 50. Typically, the distal end 46 is connected to a distal end of the balloon 42. A proximal end of the balloon 42 is typically connected to a distal end of the dual lumen tube 22. In some arrangements, a suture or sealant may be delivered through the inner tube lumen 50. The suture may control release of the detachable tip 44 when the balloon location device 14 is inserted through the second lumen 28 of the dual lumen tube 22. A space between the inner tube 38 and the second lumen 28 may define an inflation lumen through which inflation fluid is delivered from inflation port 40 to balloon 42.

The sheath 16 includes a distal end 15 and a hub 17. The sealant delivery device 12 is typically connected to the hub 17 after the balloon location device 14 is inserted through the sheath 16 to position the balloon 42 within a vessel distal of the vessel puncture. The sealant delivery device 12 is inserted through the second lumen 28 of the balloon location device 14 so that the detachable tip 44 is positioned distal of the balloon 42. In at least some arrangements, the sealant delivery device 12 is releasably connected to the balloon location device 14. When the sealant delivery device 12, balloon location device 14 and sheath 16 are assembled together as shown in FIG. 1, these components may be interconnected and move axially in tandem.

Referring now to FIGS. 2-8, the sealant mixing assembly 18 is described in further detail. The sealant mixing assembly 18 includes a first syringe 52, a second syringe 54, and an adaptor 56. The first and second syringes 52, 54 are connected to opposing ends of the adaptor 56. In at least some arrangements, the first and second syringes 52, 54 are releasably connected to the adaptor 56 so that at least one of the first and second syringes 52, 54 may be detached from the adaptor 56 after components carried by the first and second syringes 52, 54 are mixed. The first or second syringe 52, 54 may deliver the mixed components to the sealant delivery device 12 where the mixed components are further mixed and delivered to the vessel puncture.

The first syringe 52 includes first and second chambers 58, 60, first and second sealing components 62, 64 carried in the first and second chambers 58, 60, a plunger 66, and connectors 68. The first sealing component may comprise PEG or thiol. The second sealing component may comprise an activator or may be empty. At least one of the first and second sealing components 62, 64 may be stored under vacuum pressure so that when the first and second syringes 52, 54 are connected to the adaptor 56, at least one of the sealing components stored in the second syringe 54 is automatically drawn into the first syringe.

The connectors 68 may be configured to releasably connect the first syringe 52 to the adaptor 56. The connectors 68 are shown as a pair of protrusions extending from a distal end of the first syringe 52. Other types of connector features may be possible, including, for example, snap-fit features, latches, clips, brackets, or other features formed on interior or exterior surfaces of the first syringe 52. The first syringe 52 may include sealing members that provide fluid-tight seals for the first and second chambers 58, 60 (e.g., positioned at the connectors 68). The sealing members (not shown) may comprise rubber septums, foil caps, or other sealing features. The sealing members may provide sterility for the first and second sealing components 62, 64.

The first syringe 52 may be connected to the adaptor 56 in a sterile environment and then held within an enclosure such as a sterile package. This pre-assembly step may help provide a sterile environment within which the first and second sealant components 62, 64 are stored prior to connecting the adaptor 56 to the second syringe 54.

The second syringe 54 includes third and fourth chambers 70, 72 that hold third and fourth sealing components 74, 76. The second syringe 54 also includes a plunger 78, first and second needles 80, 82, a first seal member 84, a foil cap 86, and a connector 88 having connector lips 89. In one example, the third sealant component comprises acrylate and the fourth sealant component comprises an activator or nothing. In at least one example, one of the third and fourth sealant components 74, 76 may be stored under vacuum or high-pressure conditions to facilitate mixing of the sealant components held by the first and second syringes 52, 54 after connecting the first and second syringes 52, 54 to the adaptor 56.

The first and second needles 80, 82 may be coupled in flow communication with the third and fourth chambers 70, 72, respectively. The first seal member 84 may seal the first and second needles 80, 82 within the connector 88. The connector 88 may define a chamber and entrance into the chamber so that the first and second needles 80, 82 are stored in a sterile environment. The connector 88 may also define a space or chamber within which a portion of the adaptor 56 may be inserted so that the adaptor 56 is connected to the second syringe 54 and brought into flow communication with the first and second needles 80, 82. The foil cap 86 may be removably attached to the first seal member 84. The first seal member 84 and foil cap 86 may provide a sterile environment for the third and fourth sealant components 74, 76 and may limit flow of moisture into or out of the third and fourth chambers 70, 72. The foil cap 86 is typically removed prior to connecting the second syringe 54 to the adaptor 56.

The connector 88 may be configured to provide a releasable connection with the adaptor 56. In one example, the connector 88 provides a releasable connection that maintains the adaptor 56 in flow communication with the first and second needles 80, 82. The connector 88 may provide a snap-fit connection. The connector 88 may provide other types of connections and have various interfaces to provide such connections, including, for example, threaded connections, latches, clips, etc. In at least some arrangements, the connector 88 may be configured to provide a connecting function between the second syringe 54 and adaptor 56, and concurrently provide an enclosure within which the first and second needles 80, 82 are positioned for the purpose of maintaining the first and second needles 80, 82 in a sterile environment. In at least some arrangements, the first and second needles 80, 82 may be carried by the adaptor 56 instead of the second syringe 54.

The adaptor 56 includes first and second channels 100, 102, connector seats 104 for connection to the first syringe 52, locking tabs 106, support members 108, connector stops 110, a second seal member 112, and a foil cap 114. The connector seats 104 may be sized and configured to connect the adaptor 56 to the first syringe 52. In at least one example, the connectors 68 on the first syringe 52 are inserted into the connector seats 104. The first and second channels 100, 102 may be connected in flow communication with the first and second chambers 58, 60, respectively.

The locking tabs 106 may operate to release the adaptor 56 from the first syringe 52. The locking tabs 106 may be replaced with other locking or connecting features that help maintain connection of the first syringe 52 to the adaptor 56 until the operator intends to disconnect the first syringe 52 from the adaptor 56.

The support members 108 may be used as a support surface or handling feature for the user to grasp while connecting or disconnecting the first and second syringes 52, 54. The connector stops 110 may be arranged for contact with the connector lips 89 of the connector 88. In some arrangements, the connector stops 110 are provided as protrusions extending radially outward from an exterior surface of the adaptor 56. In other arrangements, the connector stops 110 may be provided as recesses, grooves, or a combination of protrusions and recesses formed on the adaptor 56 that provides an interface with the connector 88. In some arrangements, the connector stops 110 provide a permanent connection between the connector 88 and the adaptor 56, while in other arrangements the connector stops 110 provide a releasable connection between the connector 88 and the adaptor 56.

The second seal member 112 may comprise a rubber septum or other sealing material that provides a fluid-tight seal with the first and second chambers 100, 102. The second seal member 112 may be configured to be punctured or ruptured upon connecting the second syringe 54 to the adaptor 56. The foil cap 114 may be removably mounted to the second seal member 112. The foil cap 114 may limit the flow of moisture through the second seal member 112 and may provide additional sterility for the first and second channels 100, 102.

Figure 2:
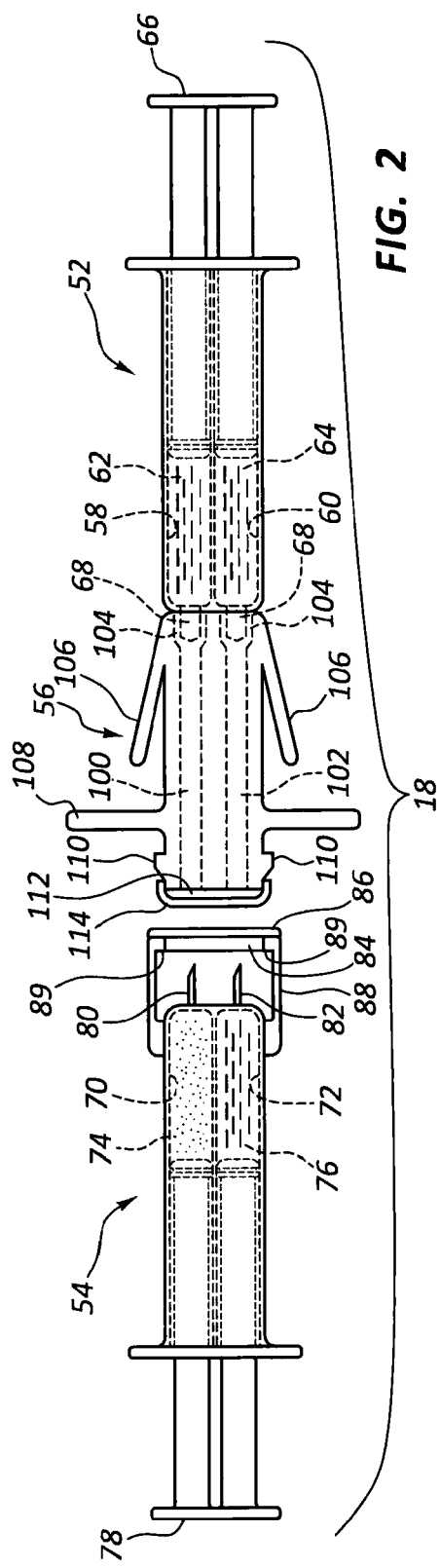
FIG. 2 is a side view of a sealant mixing assembly of the vascular closure system of FIG. 1 in a partially assembled arrangement.
Figure 3:
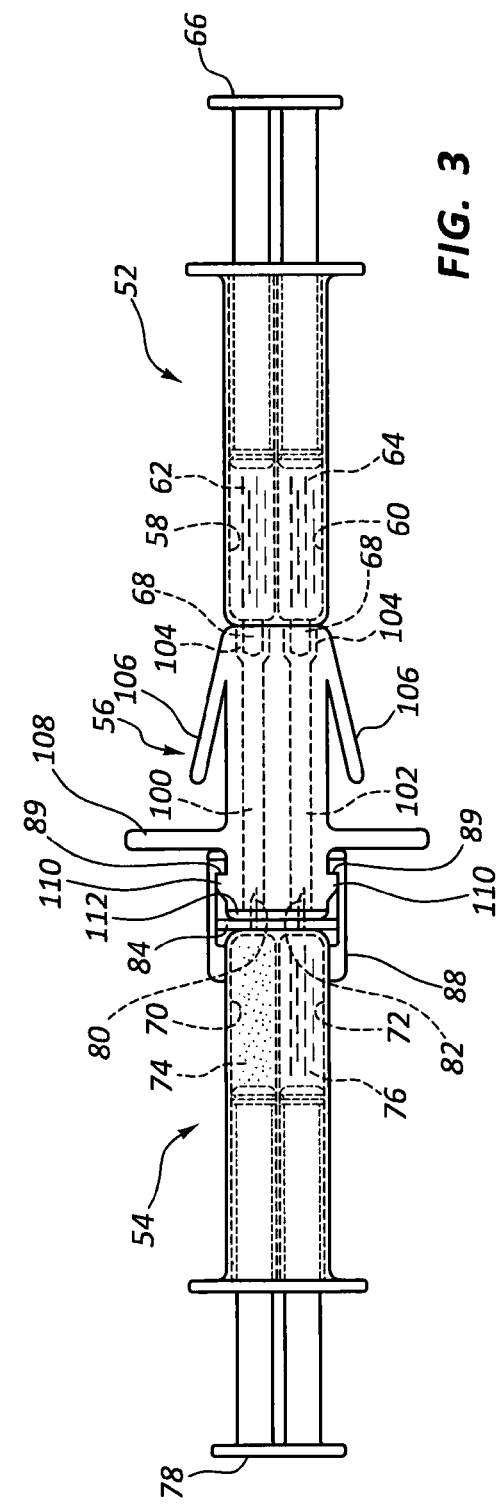
FIG. 3 shows the sealant mixing assembly of FIG. 1 in a fully assembled arrangement.

In at least one example, the adaptor 56 is first connected to the first syringe 52 as a sub-assembly as shown in FIG. 2. Typically, the first syringe 52 is releasably connected to the adaptor 56. The foil caps 86, 114 are removed from the first and second seal members 84, 112, respectively. The second syringe 54 is aligned with the adaptor 56 as shown in FIG. 2. The adaptor 56 is then inserted into the connector 88, which causes the first and second needles 80, 82 to extend through the first and second seal members 84, 112 until flow communication is provided between the first and second needles 80, 82 and the first and second channels 100, 102, respectively, as shown in FIG. 3. The connector lips 89 interface with the connector stops 110 to provide a connection between the second syringe 54 and the adaptor 56, as shown in FIG. 3. The connector 88 holds the second syringe 54 and adaptor 56 in fixed axial positions relative to each other while the first and third sealant components 62, 74, and second and fourth sealing components 64, 76 are combined in one or both of the first and second syringes 52, 54.

Referring to FIG. 4, the plunger 66 of the first syringe 52 is depressed to deliver the first and second sealing components 62, 64 through the first and second channels 100, 102 of the adaptor 56 and into the third and fourth chambers 70, 72 of the second syringe, respectively. The first and third sealing components 62, 74 are combined to form a first sealant mixture 116 in the third chamber 70. The second and fourth sealant components 64, 76 are combined to form a second sealant mixture 118 in the fourth chamber 72. The second syringe 54 may be disconnected from the adaptor 56 as shown in FIG. 6, and the second syringe 54 may be connected to the sealant delivery device 12 for delivery of the first and second sealant mixtures 116, 118 to the vessel puncture. The first and second sealant mixtures 116, 118 may be mixed and activated in the sealant delivery device 12 and after reaching the vessel puncture to provide sealing of the vessel puncture.

Alternatively, the plunger 78 may be depressed from the arrangement shown in FIG. 4 or from the arrangement of FIG. 3 to create the first and second sealant mixtures 116, 118 in the first and second chambers 58, 60 of the first syringe 52, as shown in FIG. 5. The first syringe 52 can then be disconnected from the adaptor 56 as shown in FIG. 7, and the first syringe is connected to the sealant delivery device 12 for delivery of the first and second sealant mixtures 116, 118 to the vessel puncture. The first and second sealant mixtures 116, 118 may be mixed and activated in the sealant delivery device 12 and after reaching the vessel puncture to provide sealing of the vessel puncture.

Figure 8:
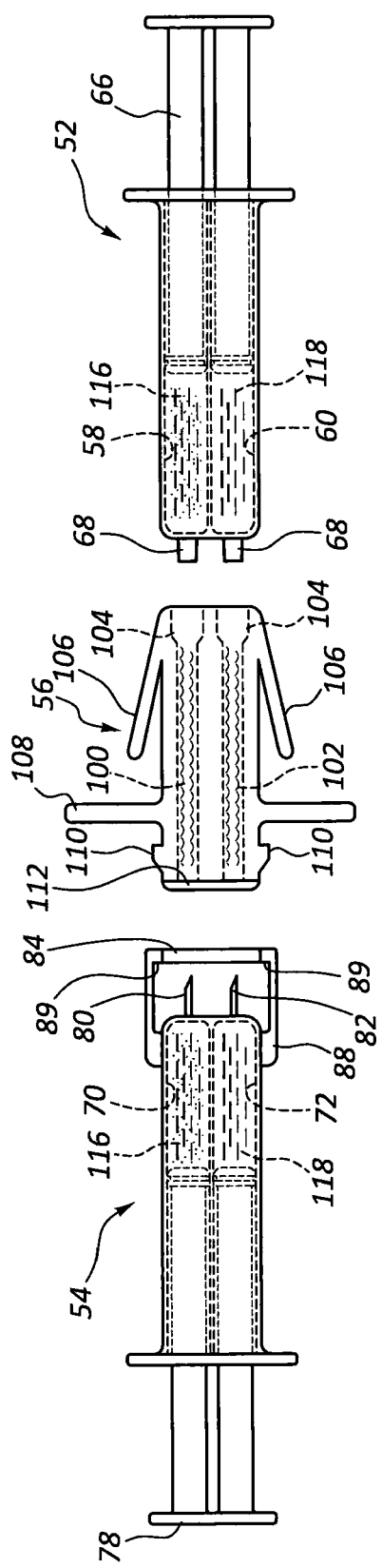
FIG. 8 shows the sealant mixing assembly of FIG. 3 with each of the syringes carrying a volume of all of the sealant components and the syringes being detached and ready for delivering the sealant components to the sealant delivery device of the vascular closure device of FIG. 1.

In a further arrangement, each of the first and second syringes 52, 54 carry at least some volume of the first and second sealant mixtures 116, 118 and then detach from the adaptor 56 as shown in FIG. 8. Each of the first and second syringes 52, 54 may be connected to separate sealant delivery devices 12 or may be used to deliver volumes of sealant to the sealant delivery device 12 at different stages of sealing a vessel puncture.

In at least some examples, one of the first and third sealant components 62, 74 comprises a powder and the other of the first and third sealant components 62, 74 comprises a liquid so that mixing of the first and third sealant components provides reconstitution of the powder. Typically, one of the second and fourth sealant components 64, 76 comprises an activator. The activator is separated from the first sealant mixture 116 until the first and second sealant mixtures 116, 118 are combined after connecting the first and second syringes 52, 54 to the sealant delivery device 12 (e.g., just prior to the delivery to the vessel puncture). In some arrangements, the sealant components used in the vascular closure system 10 are quick-set components that preferably are not activated until just prior to or as part of delivering the sealant components to the vessel puncture.

Figure 9:
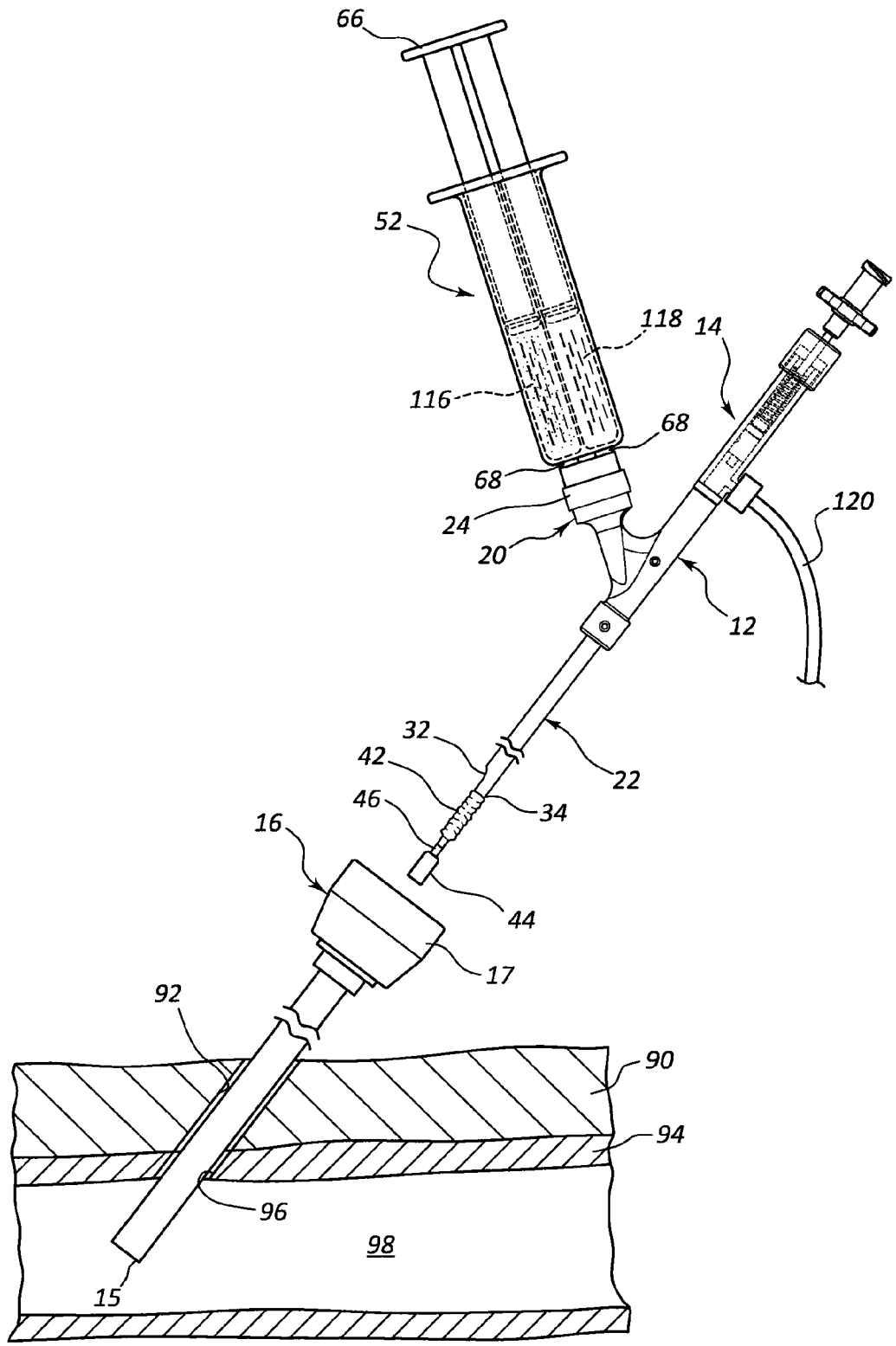
FIGS. 9-12 show one of the syringes of the sealant mixing assembly of FIGS. 2-8 in use with the vascular closure system to seal a vessel puncture in accordance with the present disclosure.

Referring now to FIGS. 9-12, an example method of operating the vascular closure system 10 to deliver sealant to a vessel puncture is shown. FIG. 9 shows the sheath 16 inserted through a tissue tract 92 of a tissue layer 90 and through a vessel puncture 96 of a vessel 94 until the distal end 15 of the sheath 16 is positioned within a vessel interior 98. The balloon location device 14 is inserted through the sealant delivery device 12 so that the balloon 42 and detachable tip 44 are positioned at a distal end of that assembly. The balloon location device 14 and sealant delivery device 12 are aligned with an entrance into the hub 17 of sheath 16, as shown in FIG. 9. One of the first and second syringes 52, 54 may be attached to the injection port 24 of the sealant delivery device 12 at any time prior to delivering the first and second sealant mixtures 116, 118 to the sealant delivery device 12.

Figure 10:
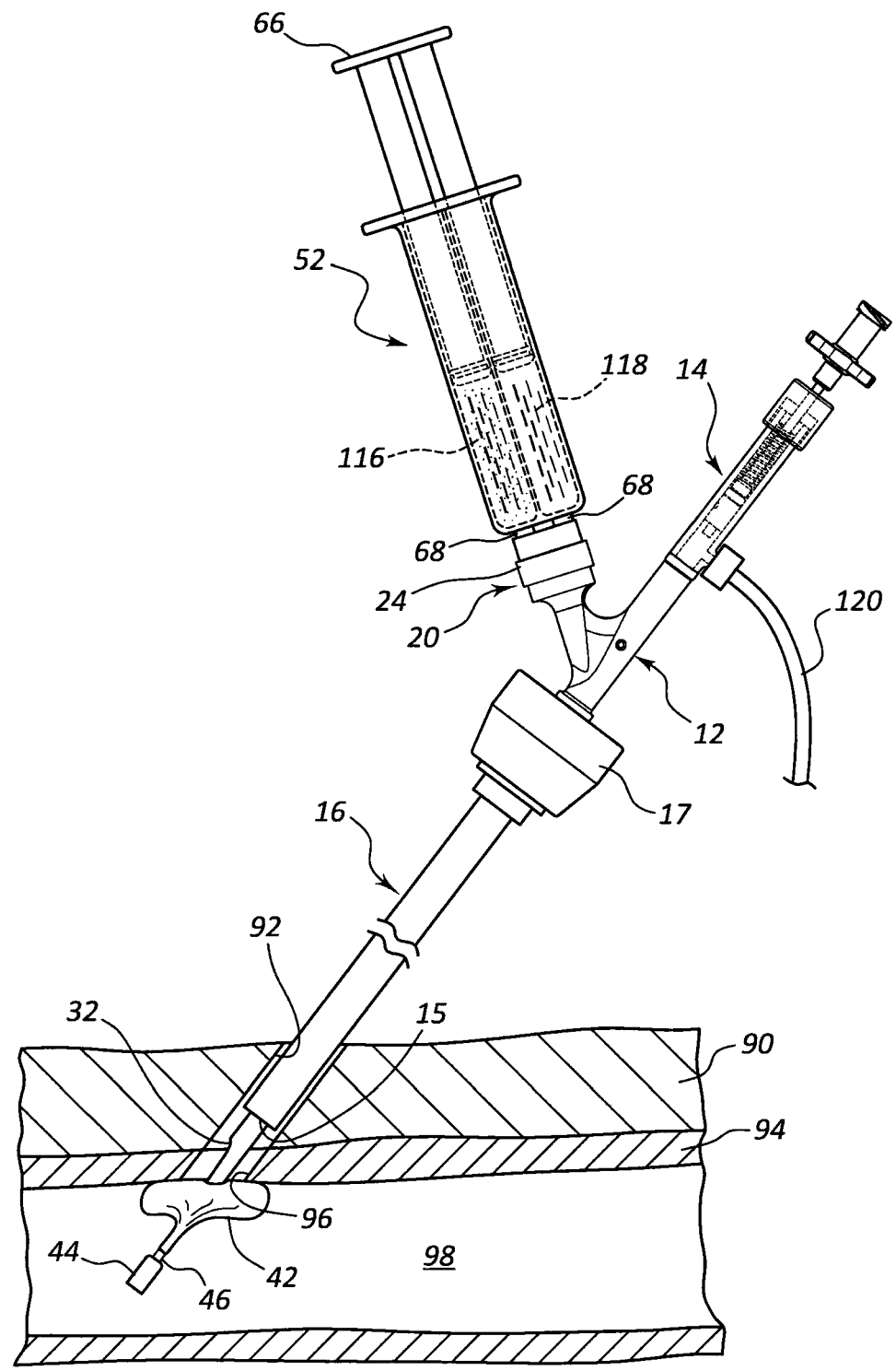

Referring to FIG. 10, the sealant delivery device 12 with balloon location device 14 is inserted through the sheath 16 until the balloon is positioned within the vessel interior 98. A volume of inflation fluid may be provided from an inflation fluid source 120 to inflate the balloon 42, as shown in FIG. 10. The inflated balloon 42 is withdrawn into contact with an interior surface of the vessel 94 adjacent to the vessel puncture 96. The balloon 42 provides temporary hemostasis for the vessel puncture 96.

Figure 11:
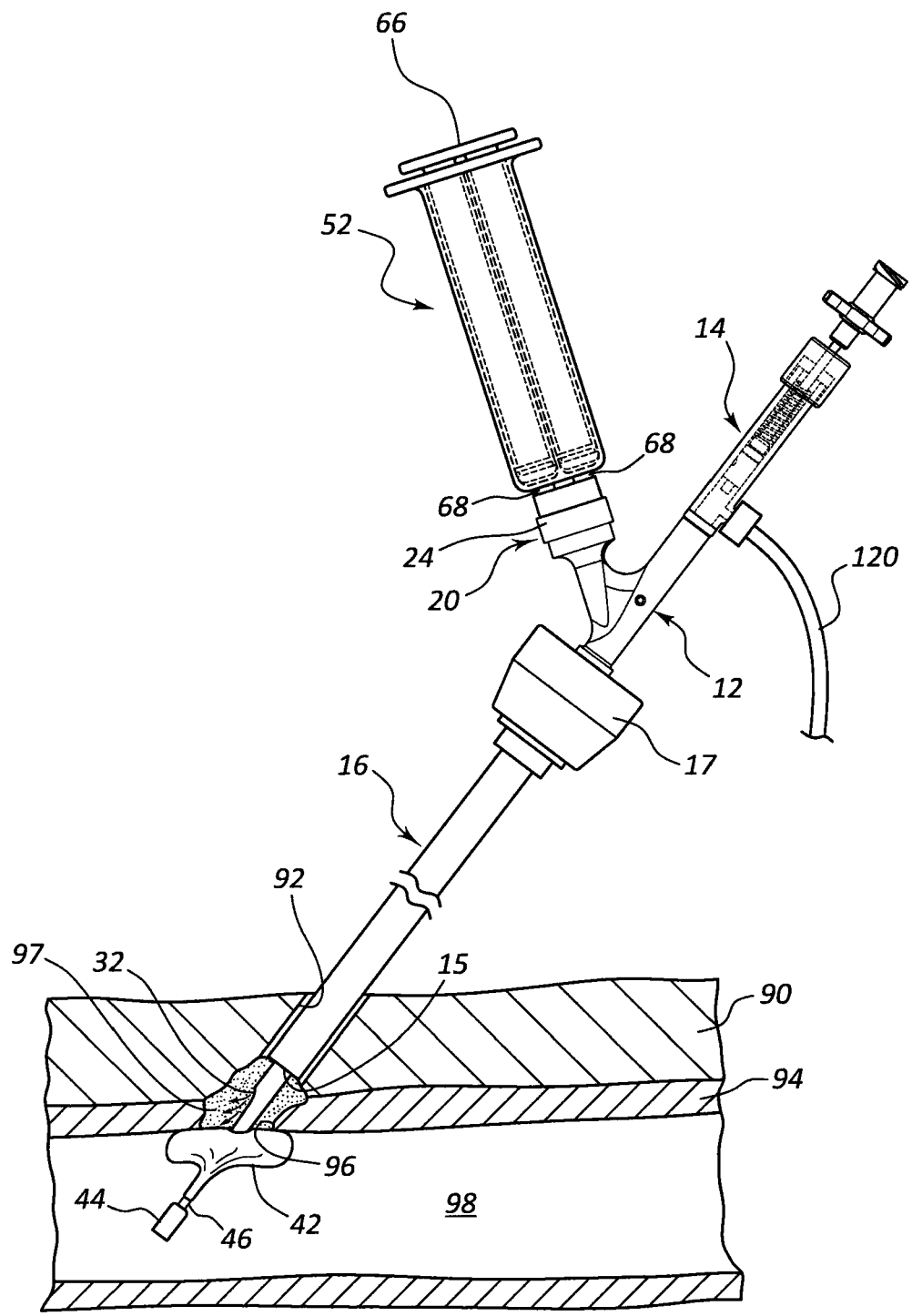

FIG. 11 shows the plunger 66 of first syringe 52 depressed to deliver the first and second sealant mixtures 116, 118 through the sealant delivery device 12 and out of the distal open end 32 and into the tissue tract 92 and vessel puncture 96. The first and second sealant mixtures 116, 118 combine to form a sealant plug 97. In at least some arrangements, the sealant plug 97 is allowed to cure into a solid or semi-solid state in which the sealant plug 97 does not flow into the vessel interior 98 upon deflation of balloon 42.

Figure 12:
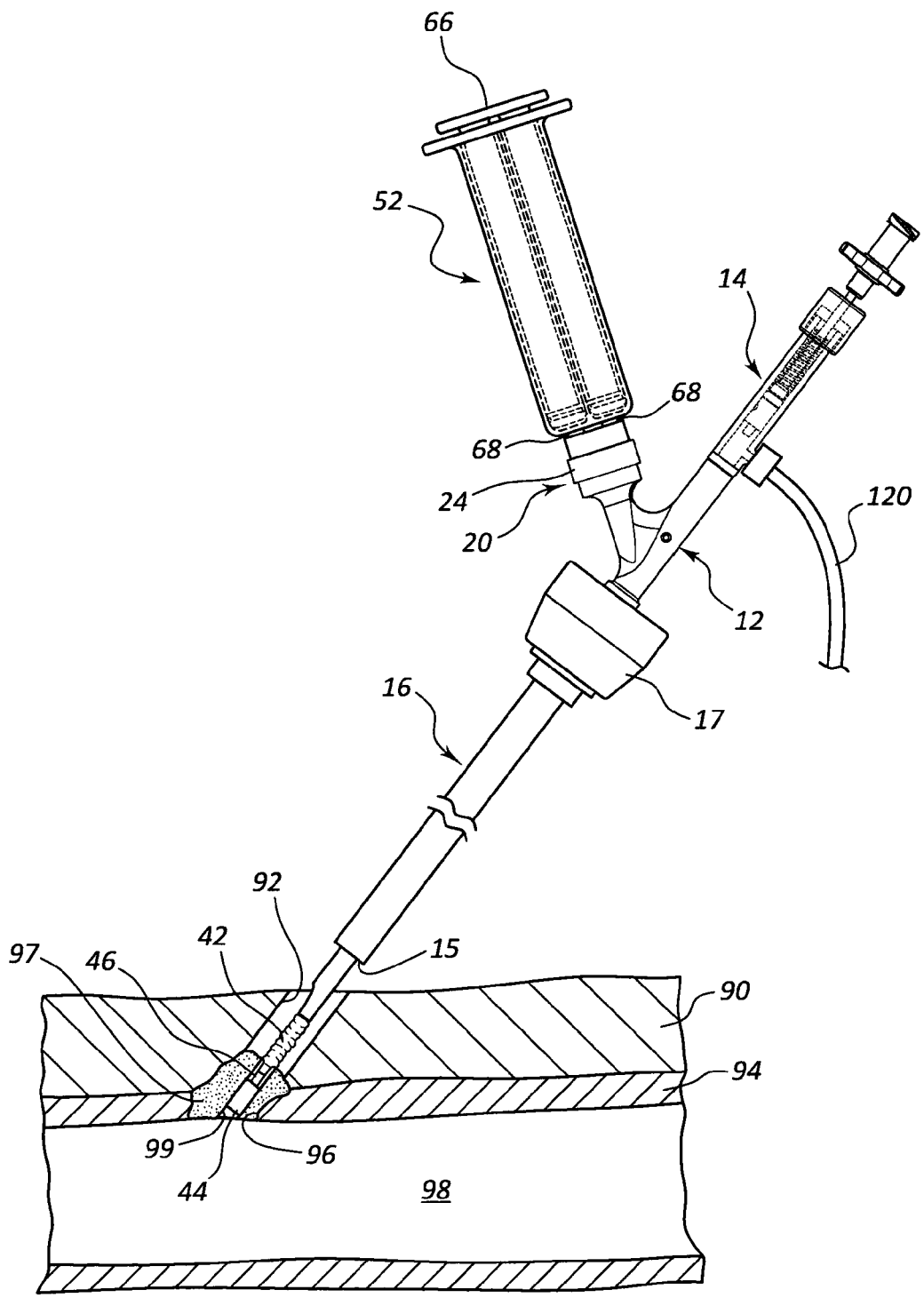

The balloon 42 is then deflated and removed through the sealant plug 97 as shown in FIG. 12. Removal of the balloon 42 through the sealant plug 97 may leave a plug channel 99 defined within the sealant plug 97. The detachable tip 44 may be detached within the plug channel 99 to further seal the vessel puncture 96. In some arrangements, a further volume of sealant is delivered from the first syringe 52 into the tissue tract 92 after detaching the detachable tip 44 to further seal the tissue tract 92. In other arrangements, the further volume of sealant is delivered through the inner tube 38 to the tissue tract 92.

In other arrangements, the same or similar interface provided between the second syringe 54 and adaptor 56 as shown in FIGS. 2-8 may be also be provided between the first syringe 52 and adaptor 56. In one example, the adaptor 56 includes a seal member at opposing ends, wherein the seal member at each end is punctured or ruptured concurrently with connecting the adaptor 56 to each of the first and second syringes 52, 54. In other arrangements, the adaptor carries at least one needle at opposing ends thereof. The needle may be retained within a sterile chamber and be accessible through a sealing member such as the first seal member 84 of the second syringe 54. The needles of the adaptor 56 may concurrently rupture the seal member and any seal members of the first and second syringes 52, 54 as part of connecting the adaptor 56 to the first and second syringes 52, 54. Providing the needles on the adaptor 56 rather than on the first and second syringes 52, 54 may permit connection interfaces on the first and second syringes 52, 54 for easier mounting to the sealant delivery device 12. In other arrangements, the sealant delivery device 12 includes a rubber septum or other seal member at the injection port 24, and the syringe carrying the first and second sealant mixtures may have at least one needle that punctures the seal member at the injection port 24.

The various examples disclosed herein provide for syringes that include first and second chambers that carry multiple sealant components. Other examples may include three or more chambers in each of the syringes or at least one chamber carrying at least one sealant component in each chamber of each syringe. The first and second syringes may have unequal numbers of chambers and carry unequal numbers of sealant components. The sealant components may be stored under various pressure conditions, such as, for example, a vacuum pressure condition or a high-pressure condition.

Some arrangements may include three or more syringes that each carries at least one sealant component. The adaptor may include interfaces for connection to two separate syringes, as shown in FIGS. 2-8. Alternatively, the adaptor can include three or more interfaces for connection to three or more syringes that each carries at least one sealant component. In one example, the adaptor provides an interface for three different syringes, wherein first and second syringes each carry at least one sealant component and the third syringe is empty. The mixed sealant components of the first and second syringes are delivered into at least one chamber of the third syringe, and the third syringe is disconnected from the adaptor and used to deliver the mixture of sealant components to the sealant delivery device 12. Many other variations on the number of syringes and the construction of the adaptor and the various interfaces there between may be possible in accordance with the present disclosure.

The sealants discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A bioadhesive mixing assembly, comprising:
   a first syringe having first and second chambers holding a first sealant component and an activator, respectively;
   a second syringe having third and fourth chambers holding a second sealant component and one of another activator or a third sealant component, respectively;
   an adapter mounted to the first syringe and comprising:
      first and second channels in flow communication with the first and second chambers;
      a first seal member providing sealed access to the first and second channels;
      at least one protrusion;
   first and second needles connected in flow communication with the third and fourth chambers;
   a connector attached to the second syringe, the connector defining a chamber, the first and second needles being positioned within the chamber, the chamber having a connector lip, the at least one protrusion of the adapter engaging the connector lip;
   a second seal member enclosing the first and second needles within the chamber of the connector;
   wherein connecting the adapter to the second syringe punctures the first and second seal members with the first and second syringes to create flow communication between the first and third chambers and the second and fourth chambers.

2. The bioadhesive mixing assembly of claim 1, wherein one of the first and second sealant components is stored under vacuum pressure.

3. The bioadhesive mixing assembly of claim 1, wherein the first and second seal members comprise a rubber septum.

4. The bioadhesive mixing assembly of claim 1, wherein the adapter and second syringe are connected together with a snap-fit connection.

5. The bioadhesive mixing assembly of claim 1, wherein flow communication is created between the first and second syringes by relative longitudinal movement between the adapter and second syringe.

6. The bioadhesive mixing assembly of claim 1, further comprising a first removable foil cap positioned on the first seal member, and a second removable foil cap positioned on the second seal member.

7. The bioadhesive mixing assembly of claim 1, wherein the first sealant component comprises acrylate, and the second sealant component comprises one of PEG and thiol.

8. The bioadhesive mixing assembly of claim 1, wherein the adapter includes at least one release tab to releasably connect the adapter to one of the first and second syringes.

9. The bioadhesive mixing assembly of claim 1, wherein operating at least one of the first and second syringes mixes the first and second sealant components together, and mixes the activator and one of the another activator or the third sealant component.

10. A vascular closure system, comprising:
    a sealant delivery device, comprising:
       a delivery tube;
       a sealant manifold;
    a sealant mixing assembly, comprising:
    a first syringe carrying at least a first sealant component;
    a second syringe carrying at least a second sealant component, the second syringe having a first needle and a second needle;
    an adapter connected to the first syringe and in flow communication with the first sealant component;
    a stop extending from the adapter;
    a connector attached to the second syringe, the connector having an end opening;
    a lip extending inward from the end opening of the connector, the lip engaging the stop of the adapter;
    a first rupturable seal carried by the adapter and configured to be ruptured upon connecting the adapter to the connector of the second syringe;
    a second rupturable seal carried by the second syringe on the connector and configured to be ruptured upon connecting the adapter to the connector of the second syringe, the first and second needles being positioned within the second rupturable seal;
    wherein the sealant mixing assembly is operable to mix the first and second sealant components, store the mixed first and second sealant components in at least one of the first and second syringes, and deliver the mixed first and second sealant components to the sealant delivery device via connection to the sealant manifold.

11. The vascular closure system of claim 10, wherein at least one of the first and second rupturable seals comprise a rubber septum.

12. The vascular closure system of claim 10, the first and second needles being configured to rupture the first and second rupturable seals upon connecting the adapter to the second syringe.

13. The vascular closure system of claim 10, wherein each of the first and second syringes stores the mixed first and second sealant components.

14. The vascular closure system of claim 10, wherein at least one of the first and second syringes carries a sealant component under vacuum.

15. The vascular closure system of claim 10, wherein the adapter and second syringe are connected with a snap-fit connection.

16. The vascular closure system of claim 10, wherein the first and second syringes are releasably connected to the adapter.

17. A method of delivering sealant to a tissue puncture, comprising:
providing a sealant delivery device and sealant mixing device, the sealant delivery device comprising a delivery tube insertable into a tissue puncture, the sealant mixing device comprising an adapter, a connector, and first and second syringes, the first syringe holding at least a first sealant component, and the second syringe holding at least a second sealant component, the second syringe having a first needle and a second needle, the connector being attached to the second syringe, the connector having an inwardly-extending lip, the adapter including a first sealing member and the connector including a second sealing member, the first and second needles being positioned within the second sealing member, the adapter including a protrusion;
connecting the adapter in fluid communication with the first syringe;
connecting the adapter to the connector of the second syringe to rupture the first and second sealing members, the lip engaging the protrusion, wherein rupturing the first and second sealing members connects the first and second syringes in flow communication to mix the first and second sealant components;
disconnecting one of the first and second syringes from the adapter, the one of the first and second syringes carrying the mixed first and second sealant components;
connecting the one of the first and second syringes in flow communication with the delivery tube;
delivering the mixed first and second sealant components through the delivery tube to the tissue puncture.

18. The method of claim 17, wherein connecting the adapter to the second syringe includes providing a snap-fit connection between the adapter and the second syringe.

19. The method of claim 17, wherein connecting the adapter to the second syringe ruptures the first and second sealing members with at least one of the first and second needles.

20. The method of claim 17, wherein the adapter is releasably connected to at least one of the first and second syringes.

21. A method of preparing bioadhesive sealant for use in sealing a tissue puncture, comprising:
providing first and second syringes, a connector, and an adapter, the first syringe carrying at least a first sealant component and the second syringe carrying at least a second sealant component, the second syringe having a first needle and a second needle, the connector being attached to the second syringe, the connector comprising a first seal and the adapter comprising a second seal, the first and second needles being positioned within the first seal;
connecting the first syringe with the adapter to provide flow communication between the adapter and the first syringe;
connecting the connector with the adapter to concurrently breach the first and second seals to create flow communication between the first and second syringes, wherein a lip on the connector engages an external protrusion on the adapter;
mixing the first and second sealant components.

22. The method of claim 21, wherein mixing the first and second sealant components includes operating at least one of the first and second syringes.

23. The method of claim 21, further comprising providing a first removable foil cap positioned on the first seal, and a second removable foil cap positioned on the second seal, and removing the first and second removable foil caps before connecting the second syringe with the adapter.

* * * * *